United States Patent [19]
Guthrie et al.

[11] Patent Number: 5,971,997
[45] Date of Patent: *Oct. 26, 1999

[54] INTRAOPERATIVE RECALIBRATION APPARATUS FOR STEREOTACTIC NAVIGATORS

[75] Inventors: Barton L. Guthrie, Birmingham, Ala.;
Eric R. Cosman, Belmont, Mass.;
Robert A. Daniels, Haverhill, Mass.;
Michael A. Cundari, Hingham, Mass.;
Christophe P. Mauge, Somerville, Mass.

[73] Assignee: Radionics, Inc., Burlington, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/803,552

[22] Filed: Feb. 20, 1997

Related U.S. Application Data

[63] Continuation of application No. 08/384,109, Feb. 3, 1995, abandoned.

[51] Int. Cl.$^6$ ................................................. A61B 19/00
[52] U.S. Cl. ............................................................. 606/130
[58] Field of Search ............................................... 606/130

[56] References Cited

U.S. PATENT DOCUMENTS

| | | | |
|---|---|---|---|
| 4,341,220 | 7/1982 | Perry | 128/630 |
| 4,386,602 | 6/1983 | Shelden et al. | 606/130 |
| 4,608,977 | 9/1986 | Brown | 128/303 |
| 4,618,978 | 10/1986 | Cosman | 378/164 |
| 4,638,798 | 1/1987 | Shelden et al. | 606/130 |
| 5,230,623 | 7/1993 | Guthrie et al. | 433/72 |
| 5,389,101 | 2/1995 | Heibrun et al. | 606/130 |

FOREIGN PATENT DOCUMENTS

| | | | |
|---|---|---|---|
| 1282623 | 12/1961 | France | 606/130 |
| 2809645 | 11/1978 | Germany | 606/130 |

*Primary Examiner*—Michael Buiz
*Assistant Examiner*—Kevin Truong
*Attorney, Agent, or Firm*—Darby & Darby P.C.

[57] ABSTRACT

This invention relates to apparatus for calibrating and recalibrating a digitized navigator or so-called frameless stereotactic instrument or device during a surgical operation. The apparatus enables calibration for the stereotactic digitizer to be recovered after sterile draping of the patient, movement of the patient's head during operation, relative movement of the patient's head and reference apparatus associated with the stereotactic digitizer, power failures, or other events which could compromise calibration of the stereotactic digitizer during the operation which would otherwise preclude continuations using the digitizer. It also provides convenient means for initial calibration or repeat calibration, should that be necessary. The apparatus is, in one embodiment, cooperatively coupled to, or coupled so as to move with, the portion of the patient's body which is being operated upon and enables the repositioning of the recalibration means after sterile draping. In exemplary embodiments, the apparatus would include a reference point structure or a reference holding structure that can be attached to, for example, a surgical head clamp in a neurosurgical operation and can be accessed for calibration positioning or calibration locationing by the digitizer during the operation. The apparatus could be removed, sterilized, and repositioned in an identical position relative to the head clamp, and therefore the patient's head during the operation, assuring that sterility and loss of calibration would not be compromised.

8 Claims, 3 Drawing Sheets

INTRAOPERATIVE RECALIBRATION APPARATUS FOR STEREOTACTIC NAVIGATORS

This application is a continuation of application(s) Ser. No. 08/384,109 filed on Feb. 3, 1995 now abandoned

BACKGROUND TO THE INVENTION

The field of so-called frameless stereotaxy, which includes use of digitized stereotactic navigators of a variety of kinds, has been well known for several years. Many types of stereotactic or so-called frameless digitizers are available, and such stereotactic navigators include mechanical operating arms, ultrasonic localizers, infrared light-tracking digitizers, magnetic digitizers, and others. These digitizers are designed to provide data relative to detection apparatus that can be used to track their position or the position of an instrument in space relative to a surgical field. For example, a surgical instrument mounted with light-emitting diodes or attached to a mechanical operating arm can send electronic signals to a computer graphic workstation which can assimilate these signals and determine the position and movement of the stereotactic navigator. Typically, to relate the position quantitatively of the stereotactic navigator to the patient's anatomy, a calibration maneuver is performed. For example, taking the case of neurosurgery, where the selected target position would be inside the brain, the patient is scanned in an imaging scanner. The image scan data is usually stacks of two-dimensional data that has been referenced into a stereotactic scanner coordinate frame by means of index markers placed on the patient's head or use of natural landmarks that are identifiable both in the image scan data and also physically on the patient's anatomy. The calibration process for the stereotactic navigator might consist of touching the instrument which holds the navigator devices to a series of three or more index marker points located on the surface of the patient's head or even contour tracings or natural anatomical landmarks on the patient's head, and by registering the electronic data in these particular calibration point positions, the stereotactic navigator can be "calibrated" relative to the patient's physical anatomy and therefore relative to the image scanner data representative of the tomographic or three-dimensional image (CT, MRI, PET, SPECT, etc.) of the patient's head stored in a computer graphic workstation. Once the calibration process is complete, then movement of the stereotactic navigator relative to the patient's anatomy will enable visualization on the computer graphic workstation of where the instrument probe is pointing towards the anatomy and inside of the anatomy. In this way, the navigator can be used to plan interventions in the brain or to visualize the internal anatomy of the brain including pathology, pre-operative planning, or intraoperative guidance to neurosurgery. This technique is now known in the state of the art.

One of the problems associated with such stereotactic navigators can occur in the sequence of the operation. For example, if markers are placed on the patient's skin during the image scanning and the patient is then brought to the operating room, he is anesthetized and put into a head clamp. Such a head clamp is shown in FIG. 1. The stereotactic navigator is then calibrated off of the positions of the index markers, and typically there are three or more of these markers located around the patient's head. By the way, these markers could be natural anatomical landmarks or the surface contour of the patient's head, for that matter. Once the calibration of the navigator is complete, the patient's head is sterile draped and the operation can begin. The navigator can then be used to point at the patient's head, and assessment can be made of the appropriate approach, for example, to a target within the head. A problem can occur, however, after sterile draping because the sterile draping will frequently cover up or totally obscure the index markers which enable the calibration in the first place, at a time when the field was not sterilely prepared. After sterile draping and the procedure begins, if for any reason, such as a power failure or movement of the navigator's interrogation system relative to the head, the navigator may be out of calibration relative to the patient's anatomy, and thus the navigator will be out of calibration with the three-dimensional data set from the image scanner. The utility of the navigator is then lost. One example of this might be power failure during the operation which, for the case of the mechanical operating arm, would shut down the readouts for the encoders which read out the position of the articulating links of the arm. Another example might be the movement of the patient's head relative to interrogation cameras in the case of light-emitting diode (LED) tracking systems of an instrument or a microscope. Yet another example of an intraoperative calibration loss would be movement of the relative position of a mechanical operating arm or camera or ultrasonic tracking system devices relative to the patient's head, which, again, would throw off the pre-calibration information relative to the navigator. All of these situations have the very undesirable effect of shutting down the use of the navigator at a time in the operation when it might be crucially needed. After sterile draping, the calibration points, be they natural landmarks or markers on the patient's skin or other localizers, cannot be accessed by the navigator since they are covered by the sterile drape, and therefore a recalibration based on these points is not feasible without breaking sterility. Breaking sterility might be impossible if a surgical opening has already been made.

It has been practice in some use of the Radionics OAS Operating Arm, after a skin incision has been made and the skull exposed, to make small drill holes or divot holes in the patient's skull surrounding the surgical opening or burr hole so that once the draping and sterile field have been achieved, access of these secondary registration or calibration points could be made, their position having been known or determined from the initial calibration step. This type of natural bony landmark recalibration process is possible to "restart" or "recalibrate" the digitizer, however, if the digitizer fails before such divots or bony landmarks can be established for reference, then there is still no way of recalibrating the navigator to the anatomy, and the navigator is of no use further.

Thus, one of the objectives of the present invention is to provide a means of recalibrating a stereotactic navigator in an intraoperative setting, and especially after a sterile draping has been made.

Another object of the present invention is to enable recalibration of a stereotactic digitizer in the event that the patient's anatomy, such as the patient's head with a head clamp on it, has moved relative to the means of tracking the digitizer, for example, moves with respect to the base of an operating arm that has been damped relative to a patient's head clamp or relative to cameras or ultrasonic detectors which are tracking stereotactic digitizers.

Another object of the present invention is to provide a means of recalibrating a stereotactic digitizer should there be a power failure or interruption of the equipment for any reason, especially between the time of initial calibration when the surgical field is unsterile and the time when the surgical field has been sterile draped and a surgical opening made.

Yet another object of the present invention is to provide a recalibration system that can be used with any type of stereotactic navigator, whether it be mechanical arm, LED optical tracking, ultrasonic tracking, magnetic tracking, etc. Another object of the present invention is to provide a recalibration device which can be moved with the patient's head in the case of neurosurgery so that it is always well established in mechanical relationship to the patient's anatomy.

Yet another object of the present invention is to have a recalibration device which can be used unsterile in a given position relative to the patient's anatomy during a calibration process and then, after sterile draping, the device can be autoclaved or otherwise sterilized during the operation and reset back onto the patient's head or head clamping means during the operation in a repeated or repeatable fashion and/or in exactly the same position as it was previously. In this context, an object of the present invention is to have a recalibration device that can be repeatedly relocated relative to a patient immobilization structure in exactly the same position so that it can be removed if it is in the way of the surgery, but can be put back on in the event that intraoperative recalibration is necessary.

The description of the invention which follows shows how these and other objectives can be achieved by it.

DESCRIPTION OF THE INVENTION

The embodiments shown below are intended as examples or illustrations of the present invention. Those skilled in the art can make variations of these examples and yet still remain within the scope of the present invention. Therefore, the examples are not meant to limit the scope of the invention described and claimed herein.

Figure 1:
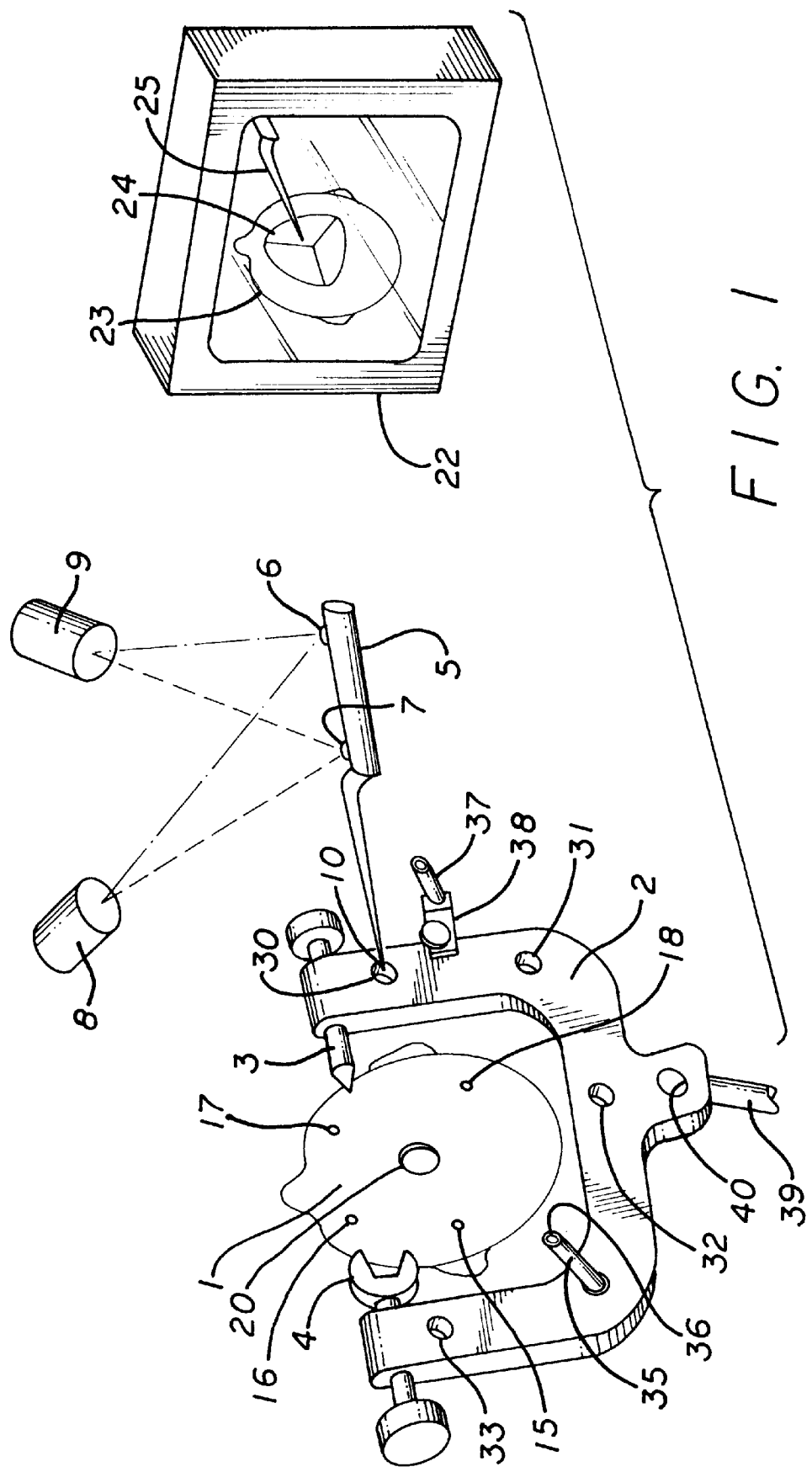
FIG. 1 shows a patient's head in a head clamp with an optical or ultrasonic digitizing probe and index marks within the head clamp that the digitized navigator can access before or after the sterilization has been made.

Referring to FIG. 1, a patient's head 1 is clamped within a surgical head damp 2 by means of securing screws 3 and 4 which stabilize onto the patient's skull and keep the patient's head 1 in a relatively securely fixed relationship to the head clamp 2. A surgical instrument 5 is shown, which, in this case, has emitters 6 and 7, which could be light-enitting diodes (LEDs), ultrasonic emitters, or other forms of energy which are being detected by detectors 8 and 9 which may be placed in a known position relative to the surgical field or have a known relationship to one another and to be so calibrated or precalibrated that they can track the position of sensors 6 and 7, and thus track the position of the surgical probe 5. Extrapolation to the probe tip 10 can easily be done geometrically so that the position of the tip and the orientation of the instrument itself can be tracked by the receivers 8 and 9 by observing only the positions of points 6 and 7. In the case of LEDs, 8 and 9 might be optical cameras. More than two optical cameras can be used in such a context. This is exemplified by, for example, the Radionics OTS Optical Tracking System. The patient's head and its anatomy can be registered with respect to a CT, MR, or other type of tomographic scan which may have been done on the patient's head prior to the operation. For example, the placement of index markers such as 15, 16, 17, and 18 on the patient's head at various positions around the periphery can be used to do such registration essentially of the physical patient's anatomy to the coordinate space of the CT scanner. Observing the index marks in the scanner in their particular slice and position within slices can reasonably calibrate the CT scan data to the physical anatomy via these point locations. By touching these points with the tip of the instrument 10 at the time of operation, one can essentially establish the calibration of the instrument 5 with respect to the patient's anatomy via these index marks and therefore establish the relationship of the instrument relative to the image scan data or the coordinate system of the scanner which had scanned the patient's anatomy. One of the objectives of this type of stereotactic navigator is then, after such calibration, to be able to point with the navigator at the patient's head and better assess where to make an entry hole such as the burr hole 20 to access anatomy within the depths of the brain, for example, a tumor which must be resected. Such a tumor can be visualized in the image scan data, its position can then be known relative to the index markers, and the index markers can be sources of calibration relative to the anatomy for the digitizer, and therefore the digitizer can be used to point at the direction of the tumor and navigate through the brain to the tumor and tumor volume. Visualization of the patient's anatomy via the image scan data can be shown on a computer graphic workstation represented by the unit 22 in FIG. 1, and a graphic rendering 23 of the patient's head showing the internal sections 24 and the position of the navigator which is approaching those sections 25. All is possible for real-time, interactive planning and surgery based on scan data and graphic representations of such scan data.

A typical procedure of setting up such an operation and calibrating the instrument relative to the anatomy would be as follows. The patient's anatomy has been pre-scanned, for example, by a CT tomographic scanner, and the image scan data from such a scan imager can be downloaded into the computer workstation 22 and renderings of the external and internal anatomy of the patient's head can be examined on the graphics display means of the computer graphic workstation for preplanning. Later the patient can be brought to the operating room and his head 1 can be clamped into the head clamp 2 as described above. Index markers such as 16, 17, and 18 may have been placed on his head prior to the scan, and those index markers seen in the image scan data then represent benchmarks or calibration points for the stereotactic navigator. With the head placed in the head clamp, as shown in FIG. 1, the navigator tip 10 can be used to touch off the physical points 15, 16, 17, and 18, and thereby the navigator is calibrated relative to the patient's anatomy, the index markers, and to the CT scan data previously done. At this phase, the patient's head is typically not sterile draped, since the index markers or position of the index markers are placed around the periphery of the patient's head and may be outside the point of surgical opening. It might be said that the index points 15, 16, 17, and 18 could be natural landmarks such as the tip of the nose, the nasion, the ear openings, or indeed the entire convexity and surface of the patient's head. These can all be used as calibration points for their stereotactic digitizer 5.

When the surgery must be done and the position of the opening decided upon by use of the navigator, typically the entire head and head damp are draped out by a sterile drape so the entire surgical field can be sterilely protected. A surgical opening such as 20 is made through the surgical drape, and access to the interior of the brain is thus possible. If the sterile drape is cloth, then the index points 15, 16, 17, and 18 will be covered up, and thus not accessible for a recalibration maneuver. When an incision is made in the scalp and the skull is exposed, a bone opening such as 20 may be made or small divot points can be made around the bone opening such as small drill holes which can be touched off by the tip 10 of the instrument 5. By touching off these points in a secondary calibration setup, they then can become reference points for recalibration. However, as stated above, if a problem arises such as a power failure between the time of covering up the patient's head with a sterile drape and the time possible to make a skin incision, all calibration might be lost, and the entire procedure restarted or the use of the navigator abandoned altogether. This is a highly undesirable state of affairs, and a solution is much needed to provide the surgeon with a way of recalibrating, even after sterile draping and even without using the drill holes in the bony opening. The drill holes in the bony opening, for example, will only give you a calibration base line which is local to the incision, and this is typically not very large. It would be better to have a base line of relocation points which is more stable and precise and yet still not compromise sterility. This is one of the objectives of the present invention. One means of doing such intraoperative calibrations is by means of indent positions such as 30, 31, 32, and 33, which are mechanical spots on the head clamp 2 itself. If the sterile drape is a thin sterile drape such as a polyethylene sheet, such indents can be seen and accessed by the tip 10 of the surgical instrument, and thus they can serve as recalibration points. For example, to repeat the setup steps in this context, the surgical instrument may have been touched off calibration landmarks 15, 16, 17, and 18, and thus calibrated to the patient's anatomy. Immediately upon doing this, and prior to sterile draping, the navigator in a recalibration setup maneuver can be touched off divot points 30, 31, 32, and 33 so as to establish a secondary set of reference points which are solidly fixed to the mechanical head clamp. As the head clamp is solidly affixed to the patient's head clamp 2, and as the head clamp 2 is solidly affixed to the patient's head 1, these represent good secondary reference points for recalibration of the probe if they are accessible after draping. As just mentioned, a thin, relatively transparent sterile drape can be used in this context, and if the points such as 30 are, for example, conical indentations in the metal of the head clamp, the thin sterile drape can contour into these conical indentations, and the point 10 of the instrument can be set down, therefore, into the conical indent with a thin drape in between and a good registration of the tip to the probe 10 can be made to the registration mark represented by 30. Thus, after such sterile draping with a thin, transparent drape, the divot points 30, 31, 32, and 33 represent touch-off points for the navigator after sterile draping and prior, during, or after making of the surgical skin incision. Should the divot points on the head clamp be too low in profile beneath the drape, an alternative means such as illustrated by the vertical post 35, which may have a divot point 36 on its top, may be set down and affixed into the head clamp through the sterile drape or be draped out around by sterile cloth and still the tip may remain sterile. For example, these may be sterilizable posts which can be put onto or attached to the head clamp after draping around to the side of the drape or underneath. This might be illustrated by the post 37, which can be clamped around the head clamp even with the sterile drape on it, illustrated by the clamp means 38. Thus, even after sterile draping, such a post can be attached to the head clamp in several positions and relocated by pin indents in the clamp so it can be positioned precisely and can be used, therefore, as relocatable elements or touch points for the stereotactic digitizer. Thus there are a variety of ways of making index spots or markings or posts or divots on or attached to the head clamp in relocatable and reproducible positions and orientations which can be touched off as secondary reference points to be used intraoperatively so as to re-establish, check, or confirm calibration of the navigator. For example, there may be one post which can be attached to the head clamp to which one can mount a sterilizable apparatus which may contain three or more conical indentations.

As another aspect of such a situation, the head clamp 2 may be attached by a shaft 39 to further head holding structures attached to the operating table. Typically, shaft 39 is on a rotatable, dampable joint such as 40 attaching itself to the head clamp. If for any reason 39 moves during the operation, or other movements of 1, 2, or other element occurs, then the calibration position established by, for example, cameras 8 and 9 during the first touch-off maneuver on index points 15, 16, 17, and 18 has been corrupted. In this situation, access to index points which are both available to be seen after sterilization and to be touched off or accessed by the probe after sterilization is required, or the probe must be recalibrated to the initial fiducials to continue. This, again, is a context where such secondary mechanical reference points are important.

Figure 2:
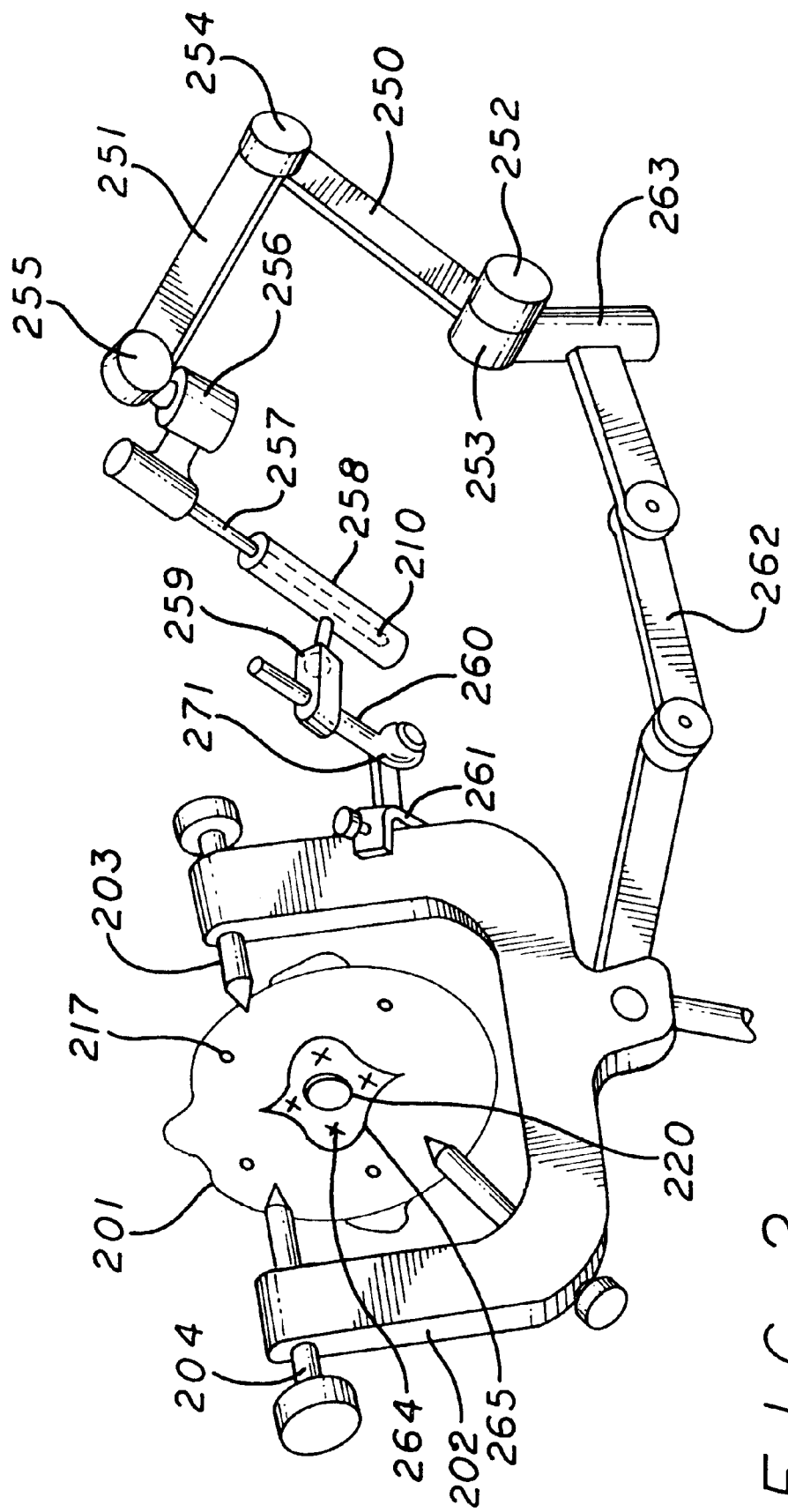
FIG. 2 shows a digitized operating arm relative to a patient's head clamped in a head clamp and a recalibration structure which can be held with respect to said head damp and having a docking or holster means in which the digitized probe can be recalibrated.

FIG. 2 shows another mechanical means for intraoperative sterile recalibration of a surgical digitizer. Again, head 201 is clamped in head clamp 202 by means of head screws 204 and 203. The index points illustrated by the point 217 can be placed on the patient's head during scanning and surgery for initial calibration. In this situation, an operating arm, which is another form of digitizer, is represented by the device on the right in FIG. 2, which has arm links 250 and 251 with double bearings 252 and 253 and intermediate rotation joint 254 and, for example, articulation joints 255 and 256, which lead to a probe such as 257. The probe is shown in this situation inside of a probe holster 258 which is attached by means of an articulating joint 259 and rod means 260 to a clamp means 261 which can be attached to the periphery of the head clamp 202. The operating arm is further attached to the head clamp by linkages represented by 262, which is attached to the base 263 of the operating arm. Typically these linkages are fixed in place in a convenient location and then the initial calibration prior to sterile draping is carried out of the operating arm system. The links and joints of the operating arm system are known in length, and the joints contain encoder structures to provide electronic readouts of the position and angle of the articulating joints and thus of the position and orientation of the tip 210 and the probe 257, which is the instrument end of the entire operating arm system. In this sense, the operating arm illustrated in FIG. 2 is analogous to the stereotactic navigator in FIG. 1, except that instead of optical or ultrasonic or magnetic coupling to detectors, the probe 257 is coupled by mechanical arms and links to the base 263 which is in turn coupled to the head clamp 202. The operating arm with its electronic readout can be coupled and inputted to a computer graphic workstation such as 21 in FIG. 1 (not shown in FIG.

2), and digitized data can be used in an entirely analogous fashion to that in FIG. 1. Intraoperatively, if there is a power shutdown or electronic interface failure between the operating arm encoders and computer graphic workstation, then the orientation and digital information from the encoders can be lost and a recalibration procedures must be instituted.

A way of recalibrating intraoperatively, as illustrated by FIG. 2, would proceed as follows. The patient, having been scanned, is set into the head clamp as described in the case of FIG. 1, and the operating arm probe 257 is touched off the reference points such as 217, and thus the arm is calibrated relative to the head and to the three-dimensional image data. At this point, and before the sterile draping is done, the clamp 261 is put onto the head clamp 202 and the rod structure 260 is put at a convenient angle, adjusted accordingly by the locking joint 271. Similarly, the orientation and angle of the holster or calibration tube or docking device 251 is oriented at a convenient angle. The probe from the operating arm 257 is inserted to a particular docking position with a depth or similar means down into or attached to the docking device 258, and the computer graphic workstation or other means is used to record or establish the encoder readings for that secondary calibration position and orientation of the probe 257. The holster may have an angular index means which enables docking of the probe or arm into it in the same position and angular orientation with respect to the probe's shaft to insure that all the encoders have the same repeated position. The storage of this calibration data in the computer then serves as a benchmark for restarting the system should there be an interruption or movement of the operating arm's base position relative to the head. The storage of this data might be done on a backup hard copy system such as a disk or magnetic tape so that even if there is a power failure, the data can be re-accessed after the power failure has resolved itself, and then the computer restarted. This means that absent any other access to reference markers such as 217, if the operating arm pointer is reinserted into the holster 258 and that has not moved relative to head clamp 202, then knowledge of the secondary calibration data referred to above can mean that the operating arm can be started up based on the initial calibration to the head through the intermediary of the secondary recalibration encoder information when the probe is in holder 258. The operating arm can be totally recalibrated in the event of a power failure if the secondary recalibration has been performed. The secondary recalibration relates coordinates of the operating arm into patient image space. The arm can restart using its manufactured zero position or the new position from the holster 258 in FIG. 2. The arm can be calibrated from set angles from 258 and thus, by referencing the points on the patient 264 and 265, can be recalibrated using the transformation maneuver. The arm can also be recalibrated from a mechanical fixture that is in the operating field as long as those points were stored in patient data spaces. Another notable point is that drill hole positions, such as the crosses represented by 264, may be placed in the skull within a region exposed within the skin incision exposure represented by the line 265. After making the incision 265, the operating arm tip 210 can be touched off these skull-based reference points which then can represent yet another recalibration data set local to the surgical opening represented by the hole 220. If a power failure occurs, the probe 257 can be put into the sterile holster 258 or the probe can then be touched off the skull reference points 264, multiplicity of them being placed around the bone opening 220, and the procedure restarted. Another eventuality which can lead to need for recalibration is that the links 261 or 263 may shift in their position relative to head clamp 202, thus throwing the operating arm system out of calibration relative to the patient's anatomy 201. This would require intraoperative recalibration, and the recalibration holster 256 could be crucial to do so if the skull surgical recalibration points such as 264 have not been made yet.

Figure 3:
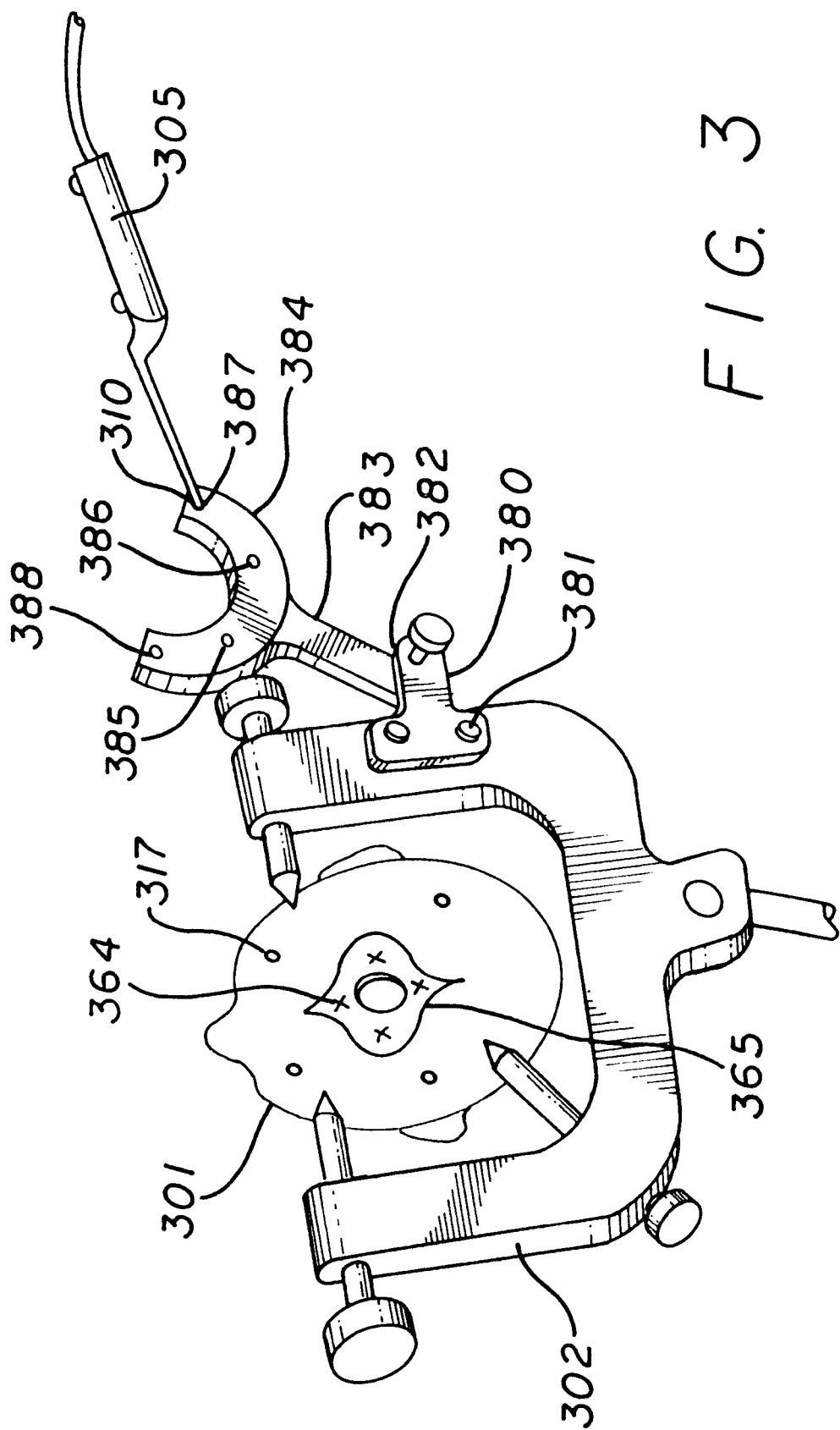
FIG. 3 shows a recalibration plate or array of index points that can be mounted repeatedly onto a head damp in an identical position, the recalibration plate having index spots which can be touched off by said stereotactic navigator so as to recalibrate itself relative to the head clamp and therefore the patient's anatomy intraoperatively.

FIG. 3 shows yet another embodiment of a recalibration means according to the present invention. Again, head clamp 302 clamps the patient's head 301 by means of clamp screws. The recalibration structure in this case is represented by a clamp 380 which can be repeatedly attached to the head clamp by indexing pins or screws 381 in known screw locations in the head clamp. The lockable joint 382 holds the arm 383 which has a yoke 384 on its top. The yoke has divot or marker points 388, 385, 386, and 387, into which the tip 310 of the surgical instrument 305 may be touched. Sterile draping can be done to the head clamp after calibration on such markers as 317 is done in the way described above. Shortly after this initial calibration and still in the non-sterile situation, the recalibration device 384 is clamped onto the ring by means of damp 380, and the stereotactic navigator 305 is used to touch its tip 310 off the various divot points such as 387, 386, 385, and 388, so as to establish a secondary coordinate system data set that is rigidly affixed to the head clamp 302, and therefore the patient's head 301. The clamp 380 may now be removed and the patient's head be sterile draped. The unsterile damp 384 may now be autoclaved, and it may be repositioned with or without the drape in place by means of pin holes, conical holes, or location docking devices which could, for example, access underneath the drape to the underside of the head clamp 302 without compromising the sterility of the overall procedure or which may be prominent enough to allow docking of the clamp even over the drape. The draping would then drape out the base of the device 380, and all that would be remaining in the sterile field above the sterile drape would be the index marker holder 384 with the divot holes in them. These could then be touched off directly with the navigator 305 for a repeatable, relocatable recalibration maneuver after sterile draping. This recalibration maneuver using the recalibration device can be interleaved or iterated with the surgical opening recalibration bone markers represented by 364 which are visible after the incision 365 has been made and can also be used for intraoperative calibration if necessary.

It is noted that, although the embodiments herein indicate surgical instruments or pointers, a wide range of such stereotactic navigators is included within the scope of this patent. For example, the probes illustrated in FIGS. 1, 2, and 3 could be surgical instruments, suction tubes, bipolar forceps, etc. for use in surgical interventions. The generic surgical probe could also refer to a microscope which is set up and adapted to be a stereotactic navigating microscope. This can be done by encoder joints of the microscope movements or by attachment of localization devices such as LEDs, ultrasonic detectors, etc., so as to make the microscope stereotactic. The microscope could be focused on various of the recalibration points established by the device of the present invention, and the microscope can be recalibrated at any time during the surgical procedure. The holster of FIG. 1, for example, could be a reticule-type tube which could be viewed through by the microscope so as to establish a direction and depth calibration in such a way that the microscope, with a single positioning maneuver, could be recalibrated back to the space of the patient's anatomy and head clamp, and therefore the imaging data, very much as the mechanical probe can be put into the holster in FIG. 2 for such a purpose. The recalibration device described here could be used in other applications in surgery as, for example, in radiation therapy where a mechanically-attached reference system can be securely fixed and secured to the patient's body for the purpose of recalibration relative to a LINAC radiation machine, for example. The recalibration device herein could also be unitized with a dynamic tracking device which contains LEDs on the same plate or structure as is contained the divots or recalibration markers. All of these concepts are included as claims as part of the present invention.

Also as part of the present invention the mechanical relocation structures such as 30, 31, 32, and 33 in FIG. 1, or 384, 385, 386, and 387 can have a known physical relationship with each other which can further be used to confirm the accuracy of the stereotactic navigator. For example, if these divots or mechanical touch points are at a known millimeter relationship or angular relationship one to the other, this could serve as an internal test of the accuracy and internal calibration of the digitizer itself. The predetermined knowledge of the relationship of these recalibration points could be inputted into the computer graphic workstation such that when a recalibration maneuver is done with the m, the work station will have a software module that tests the physical relationship of these points internally against the predetermined or known relationship of these points in a mechanical structure. Thus, the recalibration process could be consistency check or quality assurance check for the stereotactic navigator at the same time.

We note that in FIG. 2, the operating arm structure with its base 263 can be moveable with relation to the head clamp 202 so as to adjust its orientation to a more convenient position for the surgeon. If such a readjustment is made intraoperatively or accidentally during the surgery, the existence of the recalibration holster 258 or recalibration marker points such as in FIG. 1 or 3 would be very convenient for instantaneous and sterile recalibration of the operating arm. The operating arm, though attached mechanically by means of arm 262, is independently coupled to the head clamp 202 from the damping of the holster 258 to the head clamp 202. This can be significant in the sense that the operating arm, though mechanically coupled in a mechanical relationship to the head clamp 202, is not primarily coupled to the recalibration means 258. Thus the relocation or recalibration integrity of the relocation device 258 is independent of the position of the operating arm relative to the head clamp. The same could be said, for example, in FIG. 1, where the cameras 8 and 9 can be in a fixed position initially relative to the anatomy 1 and the head camp 2, however, the index points such as 30, 31, 32, and 33 are in a primarily mechanically fixed relationship relative to the head clamp, independent of the position of the cameras 8 and 9 relative to the head clamp. Thereby they serve as reliable and stable mechanical recalibration points relative to the patient's anatomy. Thus, the system of the stereotactic navigator, including not only the probe or instrument with its source means 6 and 7, but also the system of detection or digitization such as the cameras 8 and 9 are the independently coupled to the patient's anatomy from the coupling of the recalibration means so that inadvertent or deliberate movement of the stereotactic navigator referencing system will not affect the ability to recalibrate based on the recalibration mechanical structures.

In the surgical setting, as has been cited above, the mechanical contact structures, such as the divot points 30, 31, 32, 33 or the post 36 in the head clamp 2 of FIG. 1, the clamp and holster mechanism 261, 258, as attached to the head clamp 202 in FIG. 2 and the clamp and base structure 380 and 383, attached to head clamp 302 in FIG. 3, should be removable and replaceable onto the head clamp. In some situations, this remove-and-replace operation should put the structure in exactly the same orientation relative to the head clamp. Furthermore, it is helpful in some contexts to have these structures sterilizable quickly between the action of removal and re-application. Thus, in one embodiment of these inventions, they can be relocated onto the head clamp in a definably relocated position and orientation, and they are made of such materials that they can withstand steam or gas autoclaving between the act of removal and re-application. Thus, in the middle of a surgery, if sterility is compromised in any way and the ability to go on with the stereotactic navigator is in question, the mechanical recalibration element, as for example in each of the embodiments above, may be removed, sterilized quickly, and reapplied to the head damp to continue the case with the stereotactic navigator. Materials are often critical in these contexts, since not all materials can withstand steam autoclaving, and especially flash steam autoclaving. The use of metals or materials that can withstand high temperature, pressure, and water vapor are desirable.

Those skilled in the arts of stereotaxy, surgery, and mechanics can think of other variations of the present intraoperative recalibration scheme. This could involve various forms of recalibration devices, attachment means to the patient's anatomy, attachment means to patient immobilization devices such as a head clamp or nonabrasive head trays, or non-invasive or minimally invasive, relocatable head holders or body holders, etc. Various forms of surgical digitizers and navigators can be invoked. Various configurations of landmarks, docking devices, holders, holsters, combinations of docking devices and index marks can be conceived by those skilled in the art to accomplish the same intraoperative recalibration before, during, and after sterile draping. Various software can be invoked to create data banks of index marks, reference points, recalibration points, transformations between recalibration points, interface software to bring out the recalibration procedure, etc. All of these are meant to be claimed within the scope of the present invention.

Having described the embodiments of the present invention, what we therefore claim as Letters Patent are the following:

1. Apparatus for intraoperative recalibration of a stereotactic navigator with respect to a patient's anatomy comprising:

a mechanical recalibration element including a base which is adapted to be releasably secured invasively to a bony portion of said patient's anatomy while allowing intubation, said base being independent of the positioning of said surgical navigator with respect to said patient's anatomy, before and during a surgical procedure, said mechanical relocation element having definable reference structures in a fixed orientation with respect to said mechanical recalibration element which enables said surgical navigator to be recalibrated with respect to said mechanical recalibration element and thus recalibrated with respect to said patient's anatomy by mechanical contact of said surgical navigator with said definable reference structures.

2. The apparatus of claim 1 wherein:

said base comprises a surgical head clamp that can be securely attached to the patient's head, and said definable reference structures being mechanical contact structures that can be fixed with respect to said surgical head clamp and said mechanical contact structures being adapted to be contacted at definable points by said stereotactic navigator so as to reference said stereotactic navigator with respect to said surgical head clamp and therefore with respect to said patient's head.

3. The apparatus of claim 2 wherein said mechanical contact structures comprise index points on each mechanical contact structure that allow contact by the tip of said stereotactic navigator in a spatial relationship with respect to said mechanical contact structure, and therefore at a substantially well defined spatial relationship with respect to said surgical head clamp.

4. The apparatus of claim 2 wherein said mechanical contact structures can be repeatedly removed and reapplied to said base in the same position with respect to said base, and said mechanical contact structures is adapted to withstand sterilization between removal and re-application onto said base.

5. The apparatus of claim 1 wherein:

said base comprises a surgical head clamp that can be securely attached to the patient's head, and said definable reference structures comprise a mechanical docking structure that can be fixed to said surgical head clamp and that is adapted to receive, in a docking manner, at least a portion of said stereotactic navigator, and whereby when said at least a portion of said stereotactic navigator is so docked to said mechanical docking structure, said stereotactic navigator is in a reproducibly calibrated position with respect to said surgical head clamp and therefore with respect to said patient's head.

6. The apparatus of claim 1 wherein:

said base comprises a surgical head damp that can be securely attached to the patient's head and which is adapted to be cooperatively coupled to said definable reference structures so that said definable reference structures are attached to said surgical head clamp in the same position with respect to said surgical head clamp, said definable reference structures comprising a contact base having contact structures therein which can be touched by a portion of said stereotactic navigator so that said stereotactic navigator can be recalibrated in orientation with respect to said contact base and therefore recalibrated with respect to said surgical head clamp and thus said patient's head.

7. The apparatus of claim 6 wherein said contact base includes a plate and said contact structures include divot points on said plate such that when the tip of said stereotactic navigator touches sequentially said divot points, then said stereotactic navigator can thereby be calibrated in its orientation with respect to said divot points and thus said plate and thus recalibrated repeatedly with respect to said contact base, and said contact base being in a well defined, fixed relationship to said definable reference structure, said surgical navigator is thereby recalibrated to said patient's head.

8. A method for intraoperative recalibration of a stereotactic navigator with respect to a patient's anatomy during a surgical procedure comprising the steps of:

(a) releasably securing invasively a mechanical recalibration element including a base to a bony portion of said patient's anatomy while allowing intubation, said base being independent of the positioning of said surgical navigator with respect to said patient's anatomy during a surgical procedure, said mechanical relocation element having definable reference structures in a fixed orientation with respect to said mechanical relocation element which enables said surgical navigator to be recalibrated with respect to said mechanical recalibration element; and, (b) recalibrating said surgical navigator with respect to said patient's anatomy by mechanically contacting said surgical navigator to said definable reference structures.

\* \* \* \* \*